United States Patent [19]
Ideker et al.

[11] Patent Number: 5,107,834
[45] Date of Patent: Apr. 28, 1992

[54] LOW ENERGY MULTIPLE SHOCK DEFIBRILLATION/CARDIOVERSION DISCHARGE TECHNIQUE AND ELECTRODE CONFIGURATION

[75] Inventors: Raymond E. Ideker; Paul A. Guse, both of Durham, N.C.; Douglas J. Lang, Arden Hills; David K. Swanson, Roseville; Roger W. Dahl, Andover, all of Minn.

[73] Assignee: Cardiac Pacemakers, Inc., St. Paul, Minn.

[21] Appl. No.: 647,658

[22] Filed: Jan. 30, 1991

[51] Int. Cl.⁵ .............................. A61N 1/39
[52] U.S. Cl. ................................. 128/419 D
[58] Field of Search ..................... 128/419 D

[56] References Cited

U.S. PATENT DOCUMENTS

| | | | |
|---|---|---|---|
| 3,937,226 | 2/1976 | Funke | 128/419 D |
| 4,355,646 | 10/1982 | Kallok et al. | 128/786 |
| 4,548,203 | 10/1985 | Tacker, Jr. et al. | 128/419 D |
| 4,603,705 | 8/1986 | Speicher et al. | 128/786 |
| 4,637,397 | 1/1987 | Jones et al. | 128/419 D |
| 4,641,656 | 2/1987 | Smits | 128/419 D |
| 4,662,377 | 5/1987 | Heilman et al. | 128/419 D |
| 4,708,145 | 11/1987 | Tacker, Jr. et al. | 128/419 D |
| 4,727,877 | 3/1988 | Kallok | 128/419 D |
| 4,768,512 | 9/1988 | Imran | 128/419 D |
| 4,774,952 | 10/1988 | Smits | 128/419 D |
| 4,800,883 | 1/1989 | Winstrom | 128/419 D |
| 4,821,723 | 4/1989 | Baker, Jr. et al. | 128/419 D |
| 4,827,932 | 5/1989 | Ideker et al. | 128/419 D |
| 4,850,357 | 7/1989 | Bach, Jr. | 128/419 D |
| 4,953,551 | 9/1990 | Mehra et al. | 128/419 D |

*Primary Examiner*—William E. Kamm
*Assistant Examiner*—Scott M. Getzow
*Attorney, Agent, or Firm*—Fleit, Jacobson, Cohn, Price, Holman & Stern

[57] ABSTRACT

A cardioversion/defibrillation system employing a dual biphasic and multi-electrode discharge technique for effectively defibrillating the heart by creating a voltage gradient throughout substantially all of the heart which is above a critical voltage gradient while delivering a minimum energy shock. Effective cardioversion/defibrillation is accomplished by delivering two shocks to the heart. The first shock is at an energy level lower than that typically necessary to cardiovert/defibrillate the heart alone, and is applied between a first pair of cardioversion/defibrillation electrodes. The second shock is at an energy less than the first shock and is applied between a second pair of electrodes to shock the area of the myocardium provided with an inadequate voltage gradient from the first shock. The voltage gradient in the low gradient areas is boosted above the minimum gradient necessary to defibrillate. Thus, substantially the entire myocardium is depolarized by a voltage gradient above the critical voltage gradient, but with the total shock strength of the first and second shocks being substantially reduced.

23 Claims, 3 Drawing Sheets

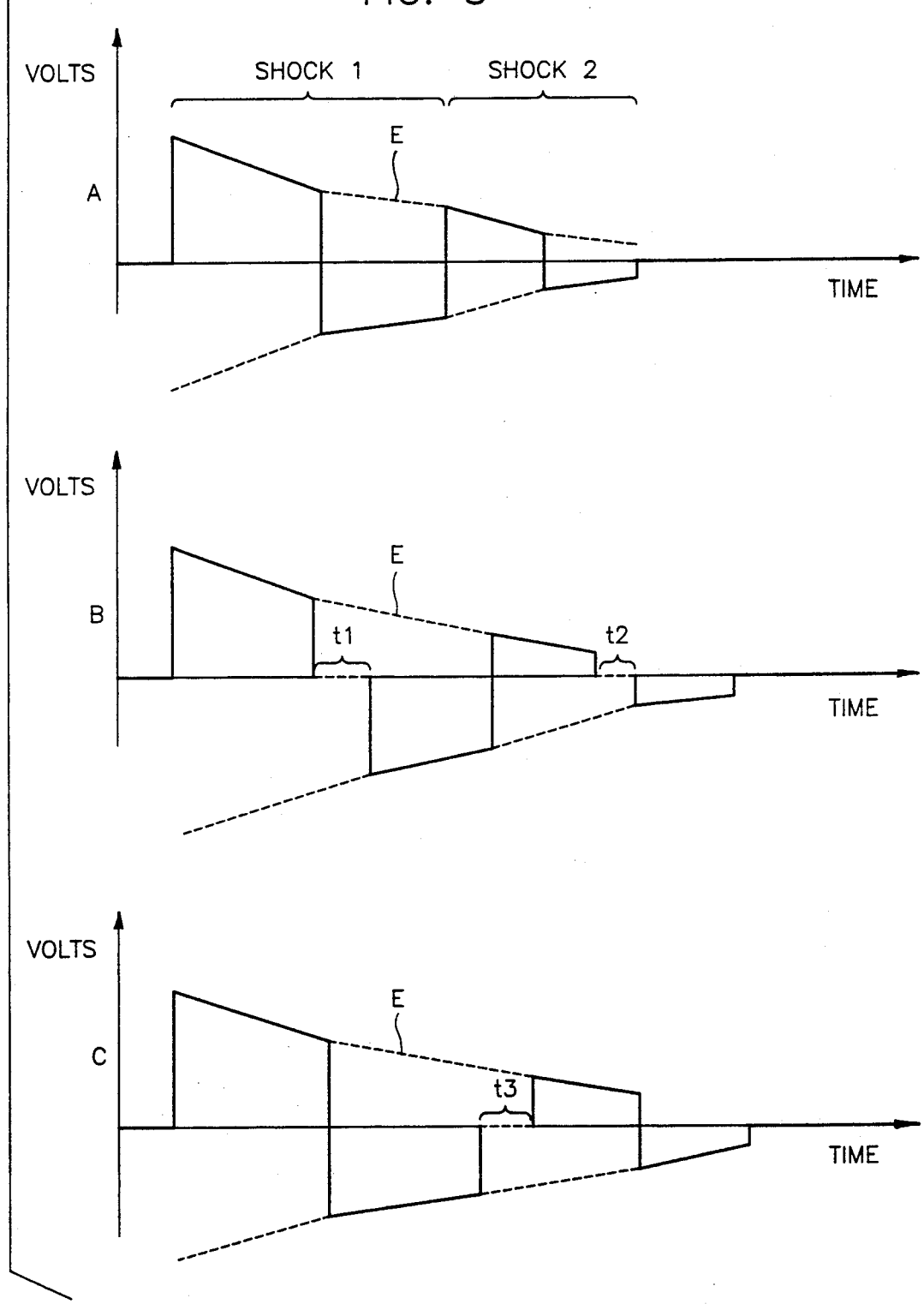

LOW ENERGY MULTIPLE SHOCK DEFIBRILLATION/CARDIOVERSION DISCHARGE TECHNIQUE AND ELECTRODE CONFIGURATION

BACKGROUND OF THE INVENTION

The present invention relates to implantable defibrillation systems, and more particularly to an implantable defibrillation system which employs a multiple electrode configuration and requires lower energies to defibrillate a heart.

There is a continuing effort in the field of implantable cardioversion/defibrillation to minimize the energy required to effectively cardiovert/defibrillate a patient's heart. Some of this effort has focused on the structure and placement of cardioversion/defibrillation electrodes to maximize the efficiency with which energy is delivered to the heart and to minimize the complexity of the surgical procedure required to implant or otherwise place the electrodes in or about the heart.

For example, U.S. Pat. No. 4,827,932 to Ideker et al. relates to epicardial implantable defibrillation patch electrodes. A first patch is designed to fit over the right ventricle and a second patch is designed to fit over the left ventricle with a substantially uniform gap being provided between borders of the patches. The gap is of sufficient width to prevent shunting of current between the two patches. The electrodes disclosed in this patent are described as achieving a uniform voltage gradient throughout the entire ventricular mass.

As another example, U.S. Pat. No. 4,603,705 to Speicher et al. discloses an intravascular multiple electrode catheter for insertion into the heart through the superior vena cava. The catheter supports a distal electrode for sensing and pacing, an intermediate electrode for sensing, pacing and cardioverting, and a proximal electrode for sensing and cardioverting. A patch electrode may be used in conjunction with the catheter.

Other efforts have been directed to particular types of cardioversion/defibrillation waveforms and techniques for delivering the waveforms to the heart. For example, U.S. Pat. Nos. 4,637,397 to Jones et al., 4,800,883 to Winstrom, and 4,821,723 to Baker, Jr. et al. are representative of patents disclosing systems and techniques for generating multi-phasic defibrillation waveforms. Another defibrillation waveform variation is disclosed in U.S. Pat. No. 4,768,512 to Imran which relates to a high-frequency truncated exponential waveform.

Elaborate defibrillation delivery techniques have been developed in an attempt to minimize the energy required by providing uniform voltage gradients throughout the myocardium. U.S. Pat. Nos. 4,548,203 and 4,708,145 to Tacker, Jr. et al., and U.S. Pat. Nos. 4,641,656 and 4,774,952 to Smits disclose a sequential orthogonal pulse delivery regime in which two pairs of opposing electrodes are implanted orthogonally to each other. A first shock is delivered between the first pair of electrodes and a second shock is delivered between the second pair of electrodes. This technique is described in these patents as equalizing the current distribution across the heart and concentrating the current in the muscular areas of the heart.

Yet another variation of the aforementioned systems is that disclosed in U.S. Pat. No. 4,727,877 to Kallok. The Kallok patent discloses a transvenous defibrillation lead system including a first catheter supporting a first electrode pair comprising a right apex ventricular electrode and a superior vena cava electrode. A second electrode pair is provided, comprising a ventricular tip electrode at the end of the first catheter and a coronary sinus electrode supported by a transvenous superior vena cava right atrial lead. A first pulse is delivered to the first pair of electrodes between the ventricular apex and the vena cava, and a preset time interval later, a second pulse is delivered to the second pair of electrodes between the ventricular apex and the coronary sinus. The patent states that a spatial summation of the sequential shocks occurs resulting in a reduction of the energy required to defibrillate the heart as compared to prior systems.

Rather than attempt to achieve uniform gradients throughout the myocardium, a technique has been developed which ensures that substantially all of the myocardium is placed above a critical voltage gradient so as to effectively countershock a fibrillating heart at low energies.

SUMMARY OF THE INVENTION

In brief, the present invention is directed to a cardioversion/defibrillation electrode configuration and discharge technique in which cardioversion/defibrillation is achieved with minimal voltage and energy. It is the desire to defibrillate the heart by creating a voltage gradient throughout substantially all of the heart which is above a critical voltage gradient while delivering a minimum energy shock. Effective cardioversion/defibrillation is accomplished with the present invention by delivering two shocks to the heart. When a shock is delivered to the heart, certain regions of the heart are defibrillated while other regions may not be defibrillated. The defibrillated regions are boosted to or above a defibrillation threshold voltage. These regions are hereinafter referred to as high voltage gradient regions. Conversely, the non-defibrillated regions are not boosted to the defibrillation threshold and are hereinafter referred to as low voltage gradient regions. In the present invention, the first shock can be at an energy level lower than that typically necessary to cardiovert-/defibrillate the entire heart, and is applied between a first pair of cardioversion/defibrillation electrodes. The second shock is at an energy less than the first shock and is applied between a second pair of electrodes to depolarize a particular area of the myocardium experiencing a low voltage gradient resulting from the first shock. Consequently, upon the delivery of the second shock, the voltage gradient in any low gradient areas resulting from the first shock is boosted above the minimum gradient necessary to defibrillate. In effect, the majority of the heart (high voltage gradient regions) is defibrillated with the first shock delivered by the first pair of electrodes and the remainder of the heart (low voltage gradient regions) is defibrillated with the second shock delivered by the second pair of electrodes.

Unlike the prior systems which attempt to achieve uniform voltage gradients through spatial summation of shocks, the present invention accepts non-uniformity and uses it as an advantage to defibrillate the heart with an overall lower energy. Thus, substantially the entire myocardium is depolarized by a voltage gradient above the critical voltage gradient, but with the total shock strength of the first and second shocks being substantially reduced.

According to a preferred embodiment of the present invention, the first and second shocks are biphasic cardioversion/defibrillation waveforms. However, the first and second shocks may be any type of defibrillation shock. A time interval may be provided between the termination of the first shock and the initiation of the second shock, and also between the phases of each biphasic shock. The entire shock cycle can be generated with a single capacitor since the second shock is at lower voltage and energy than the first. By using a single capacitor, energy that is otherwise left in the capacitor after discharge and thus wasted, is instead being used for the second shock in accordance with the present invention.

The electrode configuration used in accordance with the present invention is designed to maximize efficacy. Specifically, the electrode configuration consists primarily of a catheter electrode inserted through the superior vena cava to the right ventricle, supporting electrodes positioned in the superior vena cava, right ventricle and right ventricular outflow tract. A subcutaneous patch, coronary sinus electrode or left ventricular apical patch electrode may be provided to be discharged against one of the catheter electrodes.

It is a primary object of the present invention to cardiovert/defibrillate the heart at lower energies and without concern for the uniformity of the voltage gradient created across the heart by a cardioversion/defibrillation waveform.

The above and other objects and advantages will become more readily apparent when reference is made to the following description taken in conjunction with the accompanying drawings.

BRIEF DESCRIPTION OF THE DRAWINGS

FIGS. 3A-3C are graphic plotdiagrams of defibrillation/cardioversion waveforms used in the defibrillation/cardioversion system of the present invention.

DETAILED DESCRIPTION OF THE DRAWINGS

Figure 1:
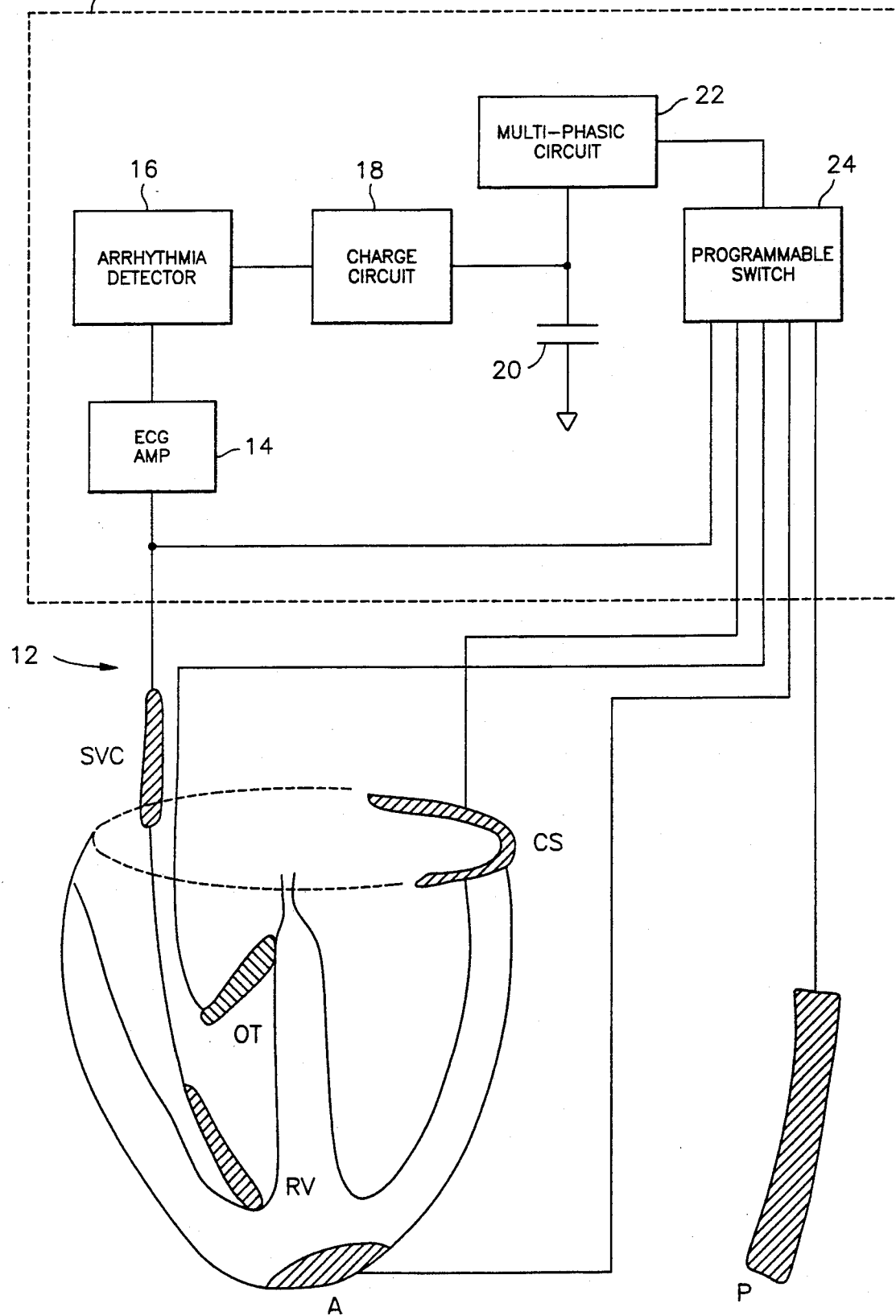
FIG. 1 is a schematic diagram illustrating the low energy defibrillation/cardioversion system according to the present invention.

Referring first to FIG. 1, the defibrillation/cardioversion system according to the present invention is shown generally comprising an electronic circuitry portion 10 and an implantable lead configuration 12. The electronic circuitry portion 10 is implantable and comprises several components well known in the art. Specifically, an ECG amplifier 14 is provided for amplifying sensed cardiac signals. The amplified cardiac signals are fed to an arrhythmia detector 16 which analyzes the electrical cardiac activity and determines if and what type of arrhythmia exists. The arrhythmia detector 16 may be one of several types known in the art and preferably is capable of distinguishing between high rate malignant tachycardias and ventricular fibrillation so as to deliver lower energy shocks in the former case than those to be delivered in the latter case. A capacitor charging circuit 18 (also known as an invertor circuit) is provided which in response to the arrhythmia detector, supplies a charging current to the capacitor 20 connected thereto.

The discharge of the capacitor 20 is controlled by a multi-phasic circuit 22. The biphasic pulse generating circuit disclosed in U.S. Pat. No. 4,850,357 may, for example, be used as the multi-phasic circuit 22. The capacitor 20 is connected to a programmable switch 24 which controls the destination of the defibrillation waveform generated by the multi-phasic circuit 22 in conjunction with the capacitor 20. The programmable switch 24 is connected to each of the electrodes shown in FIG. 1 forming part of the electrode configuration 12.

Figure 2:
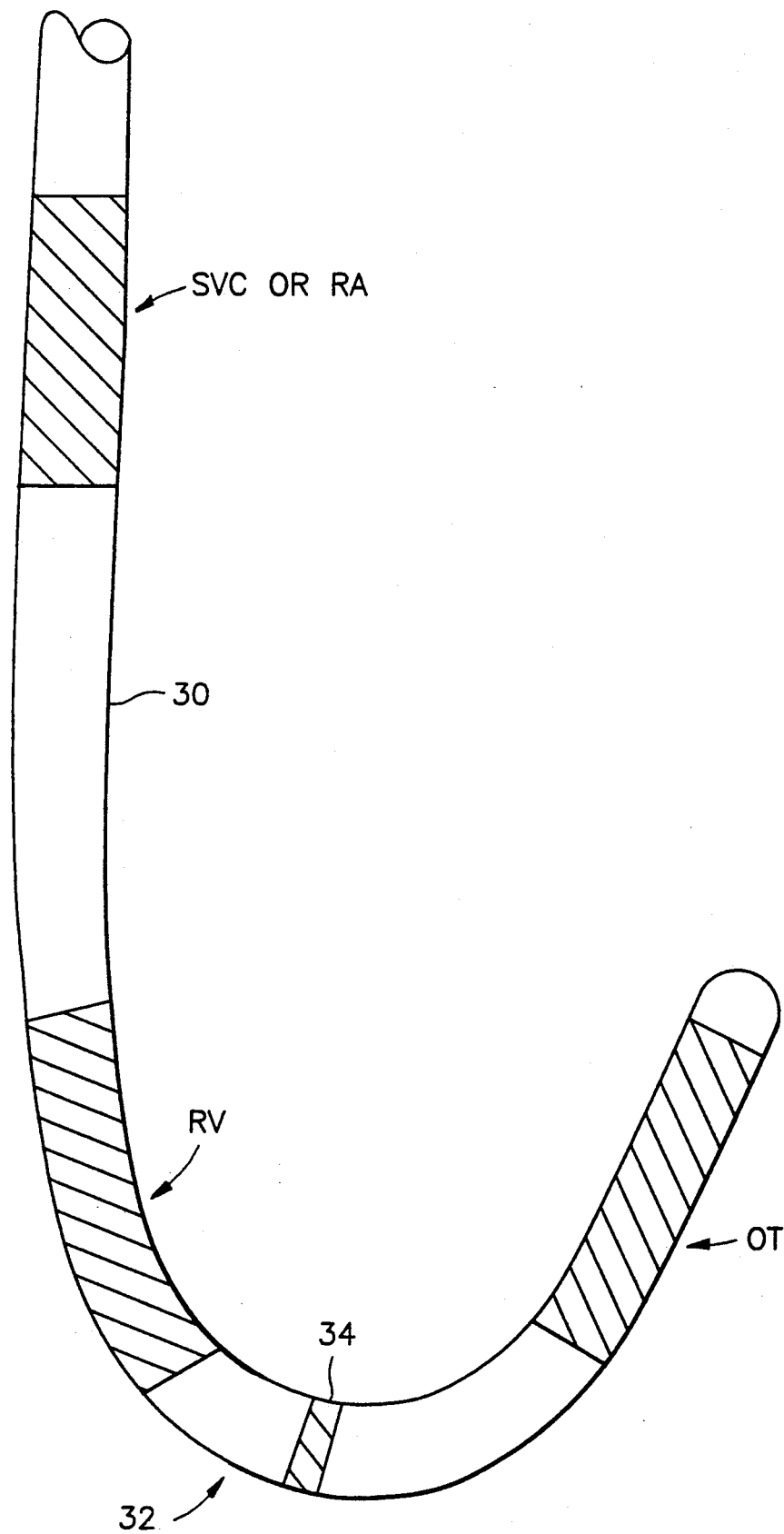
FIG. 2 is a schematic view of a single lead supporting multiple electrodes used in accordance with the present invention.

The electrode configuration 12 is a substantially non-thoracotomy multi-electrode configuration or multiple single electrode lead system as known in the industry. Four catheter mounted electrodes are provided, one catheter supporting a distal electrode positioned in the right ventricular outflow tract (OT), a proximal electrode positioned in the superior vena cava (SVC) or right atrium (RA) (not shown) and an intermediate electrode positioned in the right ventricular apex (RV). As shown in FIG. 2, the SVC or RA, RV and OT electrodes may be supported on a single intravascular catheter lead. The SVC or RA electrodes are positioned on a more proximal portion of the catheter lead body 30. The RV and OT electrodes are positioned on opposite sides of a J-shaped bend 32 at the distal end of the lead body. Each of the electrodes is connected through separate electrical conductors (contained within the catheter lead body 30) to the programmable switch 24. Furthermore, a sensing ring 34 is provided at the distal end of the catheter lead body 30 for sensing the electrical activity of the heart.

A second lead is inserted into the coronary sinus and supports an electrode (CS). This lead is a small diameter single chamber defibrillation catheter lead minus a pacing tip, or may be a narrow patch electrode. The non-catheter electrodes may include one or both of an apical patch electrode (A) mounted over the left ventricular apex and a subcutaneous patch electrode (P) positioned beneath the skin outside the thoracic cavity. Each of the electrodes shown in FIG. 1 is connected to the programmable switch 24. Placement of the electrodes is an important aspect of the present invention.

Electrode placement preferably is determined in the laboratory by mapping studies, which can provide general information about the overall typical patient population. Such generalized mapping studies are performed to determine typical voltage gradients across the myocardium in response to various electrode shock configurations, and hence, to show preferred electrode configuration and placement outside the operating room. This procedure is described in more detail in an article by Tang et al. entitled "Measurement of Defibrillation Shock Potential Distributions and Activation Sequences of the Heart in Three Dimensions", Proceedings of IEEE, vol. 76, 1988, pages 1176-1186. Recording electrodes or probes are inserted into the atria, ventricles and intraventricular septum to record from many sites (e.g. 128) throughout the heart. A shock is delivered to the heart between a pair of electrodes. The signals from the recording electrodes are routed to a computer assisted mapping system capable of processing the 128 channels simultaneously. Computer assisted mapping is known in the art. See, for example, the article to Smith et al. entitled "Computer Techniques for Epicardial and Endocardial Mapping", Progress of Cardiovascular Discovery, vol. 26, 1983, pages 15-32. The localized potential gradients from the shock between electrode pairs are calculated by a method developed by Clayton et al. and described in his article entitled "Measured and Calculated Epicardial Potentials and Gradients Resulting From Transthoracic Stimulation", 1987 Ph.D. Dissertation, Duke University, Durham, N.C.

The mapping studies are performed on representative patients (or animals) to determine, as an average, the localized high and low voltage gradient regions resulting from the discharge between the pair of electrodes in the mapping study. On the basis of these mapping studies, and according to the present invention, a first pair of electrodes is implanted on or about the heart for discharging substantially throughout all of the heart. A second pair of electrodes is implanted on or about the heart for discharging through the local region of the heart corresponding to the expected low voltage gradient area resulting from the shock between the first pair of electrodes, as determined from the mapping studies. Thus, the positions of both pairs of electrodes are determined from the mapping studies. (The term "on or about the heart" is meant to include on the surface, in the region such as subcutaneously, and within the heart.) In other words, the first pair of electrodes is implanted and will have associated therewith regions of high and low localized voltage gradients resulting from discharge therebetween. The second pair of electrodes is implanted to capture (raise above a critical defibrillating threshold) the localized low gradient areas with respect to the discharge distribution of the first pair of electrodes. It is to be understood that the term "pair" can be generalized to mean "set"; that is, more than two electrodes.

According to the present invention, the programmable switch 24 controls the destination of each phase of the waveform generated by the multi-phasic circuit 22 and discharged by the capacitor 20 so that the electrodes of a first pair (or combination) of the electrodes are discharged against each other during a first biphasic shock and the electrodes of a second pair or combination of electrodes are discharged against each other during a second biphasic shock. It is known that an arrhythmic heart can be defibrillated if substantially all of the heart is above a critical voltage gradient. However, non-uniformity in the voltage gradient throughout the heart created by the fields developed between the shocking electrodes is accepted and actually used as an advantage in accordance with the present invention. That is, the first shock between the first pair of electrodes creates regions in the heart where the current density is higher than that in others; and the first shock therefore captures (defibrillates) certain areas of the myocardium experiencing high (i.e., above threshold) current density as a result of the first shock, while failing to capture other predictable areas of the myocardium experiencing low (i.e., below threshold) voltage gradients. Through the mapping studies, the localized low voltage gradient areas are known relative to the configuration and placement of the first pair of discharging electrodes. The second shock can, therefore, be at a lower energy by delivering the second shock between the second pair of electrodes which are positioned to deliver energy mainly to the localized low voltage gradient areas not captured by the first shock delivered between the first pair of electrodes. As a result, the overall energy of the first and second shocks can be lowered substantially, while still creating voltage gradients throughout the heart which are above threshold and hence will convert the arrhythmia.

Shown in FIG. 3A is a dual biphasic waveform used in conjunction with the electrode configuration shown in FIG. 1. The first shock (Shock 1) reaches a higher voltage than the second shock (Shock 2) but is still lower than that necessary to cardiovert the heart alone. Several discharge sequences are possible with the electrode configurations shown in FIG. 1. Set forth below is a table illustrating possible combinations used in dogs. In this example, the subcutaneous patch P has a surface area of 41 sq. cm. and the apical electrode A has a surface area of 4.3 sq. cm. The single biphasic waveform used for a comparison with the dual biphasic waveforms was 5.5 msecs for each phase. The dual biphasic waveforms are 3.5 msecs for the first phase and 2 msecs for the second phase. A single 150 microfarad capacitor was used in this experiment.

| | DUAL BIPHASIC WAVEFORMS SHOCK 1/SHOCK 2 | | | |
|---|---|---|---|---|
| DFT | RV-P | RV-P/A-OT | RV-P/A-CS | SVC-RV/A-OT |
| VOLTS | 377 | 208 | 258 | 239 |
| JOULES | 9.4 | 2.7 | 4.4 | 3.9 |
| AMPS | 5.2 | 2.7 | 3.5 | 4.0 |

It is readily seen from this table that the dual biphasic waveforms produce a significantly lower defibrillation threshold (DFT) than a single biphasic waveform.

FIG. 3B illustrates another type of dual biphasic waveform in accordance with the present invention. This waveform includes a programmable time delay t1 and t2 between the phases of each biphasic portion. It has been found that a biphasic waveform with a delay of a few milliseconds, for example 2-6 milliseconds, provides for an effective defibrillation waveform.

FIG. 3C illustrates yet another type of dual biphasic waveform in accordance with the present invention. A time programmable time interval t3 is provided between the biphasic shocks. It has been found that an interval in the range of 1-10 milliseconds provides an effective defibrillation waveform.

Each of the waveforms shown in FIGS. 3A-3C is generated from the exponentially decaying voltage envelope E of a single capacitor. As a result, the second shock, shock 2 (which is desirably lower in voltage and energy) is a natural consequence of the discharge voltage waveform of the capacitor. Essentially, the charge remaining on the capacitor after the first shock is used for the second shock. There is, therefore, no need to charge another capacitor or recharge the same capacitor for the second shock. Rather, the energy used to generate the first and second shocks can be developed from the same capacitor, being discharged once, with minimal waste of energy that would normally remain in the capacitor. Finally, it is considered within the spirit and scope of the present invention to employ the present inventive technique with any type of defibrillation pulse whereby the first pulse delivered to the first pair of electrodes is of greater energy than the second pulse delivered to the second pair of electrodes.

The above description is intended by way of example only and is not intended to limit the present invention in any way except as set forth in the following claims.

We claim:
1. A system for cardioverting/defibrillating the heart of a patient comprising:
   arrhythmia detection means for detecting the occurrence of an arrhythmia;

capacitor means for storing electrical energy to be discharged to the heart;

a first pair of discharge electrodes implanted on or about the heart for discharging through the heart;

a second pair of discharge electrodes implanted on or about the heart for discharging through a local region of the heart known to experience a low local voltage gradient in a known discharge distribution resulting from discharge of the first pair of discharge electrodes;

means for charging the capacitor means to a voltage level;

circuit means connected to the capacitor means for discharging the capacitor means to generate first and second defibrillation pulses, the first defibrillation pulse being of a higher level than the second defibrillation pulse; and switch means connected to the circuit means and each of said discharge electrodes for delivering the first defibrillation pulse to the heart via the first pair of discharge electrodes and delivering the second defibrillation pulse to the heart via the second pair of discharge electrodes.

2. The system of claim 1, wherein said circuit means generates said first defibrillation pulse at an energy level which is lower than that necessary to cardiovert/defibrillate the heart alone.

3. The system of claim 2, wherein said switch means is programmable to deliver said second defibrillation pulse to said second pair of discharge electrodes subsequent the delivery of the first defibrillation pulse to the first pair of discharge electrodes.

4. The system of claim 2, wherein the first pair of discharge electrodes comprises a first electrode implanted in the right atrium and a second electrode implanted in the right ventricle, and the second pair of discharge electrodes comprises a first electrode positioned on the ventricular apex and a second electrode positioned in the right ventricular outflow tract.

5. The system of claim 1, wherein said circuit means is a multi-phasic circuit for producing said first and second defibrillation pulses as first and second biphasic defibrillation pulses.

6. The system of claim 5, wherein said multi-phasic circuit provides a predetermined period of time separating the first biphasic defibrillation pulse and the second biphasic defibrillation pulse.

7. The system of claim 5, wherein said multi-phasic circuit means provides a predetermined period of time between each phase of the first and second biphasic defibrillation pulses.

8. The system of claim 1, wherein the first pair of discharge electrodes comprises a first electrode positioned in the right ventricle and a second electrode positioned subcutaneously in the body of the patient outside the thoracic cavity, and the second pair of discharge electrodes comprises a first electrode implanted on the ventricular apex and a second electrode positioned in the right ventricular outflow tract.

9. The system of claim 1, wherein the first pair of discharge electrodes comprises a first electrode positioned in the right ventricle and a second electrode positioned subcutaneously in the body of the patient outside the thoracic cavity, and the second pair of discharge electrodes comprises a first electrode implanted on the ventricular apex and a second electrode positioned in the coronary sinus.

10. The system of claim 1, wherein the first pair of discharge electrodes comprises a first electrode implanted in the superior vena cava and a second electrode implanted in the right ventricle, and the second pair of discharge electrodes comprises a first electrode positioned on the ventricular apex and a second electrode positioned in the right ventricular outflow tract.

11. The system of claim 1, wherein both electrodes of the first pair of discharge electrodes and one of the electrodes of the second pair of discharge electrodes are supported by a single intravascular catheter lead.

12. The system of claim 1, wherein said capacitor means is a single capacitor.

13. A method for cardioverting/defibrillating the heart of a patient comprising the steps of:

implanting a first pair of electrodes on or about the heart for discharging through the heart;

implanting a second pair of electrodes on or about the heart for discharging through a local region of the heart known to experience a low local voltage gradient in a known discharge distribution resulting from the discharge of the first pair of discharge electrodes;

charging a capacitor to a voltage level;

discharging the capacitor to generate first and second defibrillation pulses, the first defibrillation pulse being of a higher level than the second defibrillation pulse; and delivering the first defibrillation pulse to the heart via the first pair of electrodes and delivering the second defibrillation pulse to the heart via the second pair of electrodes.

14. The method of claim 13, wherein the known discharge distribution resulting from the first pair and second pair of discharge electrodes is determined through mapping studies.

15. The method of claim 13, wherein the step of discharging the capacitor to generate said first and second defibrillation pulses generates such pulses as first and second biphasic defibrillation pulses.

16. The method of claim 15, and further comprising the step of providing a period of time between the beginning of the second biphasic defibrillation pulse and the end of the first biphasic defibrillation pulse.

17. The method of claim 15, and further comprising the step of providing a period of time between each phase of said first and second biphasic defibrillation pulses.

18. The method of claim 13, and further comprising the step of providing a period of time between the beginning of the second defibrillation pulse and the end of the first defibrillation pulse.

19. A system for cardioverting/defibrillating the heart of a patient comprising:

arrhythmia detection means for detecting the occurrence of an arrhythmia;

capacitor means for storing electrical energy to be discharged to the heart;

a first discharge electrode implanted in the right ventricular region of the heart;

a subcutaneous patch electrode implanted outside the thoracic cavity;

a second discharge electrode implanted on the ventricular apex of the heart;

a third discharge electrode implanted in the right ventricular outflow tract of the heart;

means for charging the capacitor means to a voltage level;

circuit means connected to the capacitor means for discharging the capacitor means to generate first and second biphasic defibrillation pulses, the first biphasic defibrillation pulse being of a higher level than the second biphasic defibrillation pulse but lower than that necessary to cardiovert/defibrillate the heart alone; and switch means connected to the circuit means and each of said discharge electrodes and subcutaneous patch electrode for delivering the first biphasic defibrillation pulse to the heart between the first discharge electrode and the subcutaneous patch electrode and delivering the second biphasic defibrillation pulse to the heart between the second discharge electrode and the third discharge electrode.

20. A system for cardioverting/defibrillating the heart of a patient comprising:

arrhythmia detection means for detecting the occurrence of an arrhythmia;

capacitor means for storing electrical energy to be discharged to the heart;

a first pair of discharge electrodes implanted on or about the heart for discharging through the heart;

a second pair of discharge electrodes implanted on or about the heart for discharging through a local region of the heart known to experience a low local voltage gradient in a known discharge distribution resulting from discharge of the first pair of electrodes;

means for charging the capacitor means to a voltage level;

multi-phasic circuit means connected to the capacitor for discharging the capacitor to generate first and second biphasic defibrillation pulses, the first biphasic defibrillation pulse being of a higher level than the second biphasic defibrillation pulse but lower than that necessary to cardiovert/defibrillate the heart alone; and programmable switch means connected to the multi-phasic circuit means and each of said discharge electrodes for delivering the first biphasic defibrillation pulse to the heart via the first pair of discharge electrodes and delivering the second biphasic defibrillation pulse to the heart via the second pair of discharge electrodes.

21. The system of claim 20, wherein said multi-phasic circuit provides a predetermined period of time separating the first biphasic defibrillation pulse and the second biphasic defibrillation pulse.

22. The system of claim 20, wherein said multi-phasic circuit means provides a predetermined period of time between each phase of the first and second biphasic defibrillation pulses.

23. A system for cardioverting/defibrillating the heart of a patient comprising:

arrhythmia detection means for detecting the occurrence of an arrhythmia;

a capacitor for storing electrical energy to be discharged to the heart;

an intravascular catheter lead inserted through the vena cava of the heart and supporting a first discharge electrode positioned in the superior vena cava, a second discharge electrode positioned in the right ventricle and a third discharge electrode positioned within the right ventricular outflow tract;

a fourth discharge electrode implanted on the ventricular apex;

means for charging the single capacitor to a voltage level;

multi-phasic circuit means connected to the single capacitor for generating first and second biphasic defibrillation pulses, the first biphasic defibrillation pulse being of a higher level than the second biphasic defibrillation pulse but lower than that necessary to cardiovert/defibrillate the heart alone; and programmable switch means connected to the multi-phasic circuit means and each of said discharge electrodes and subcutaneous patch electrode for delivering the first biphasic defibrillation pulse to the heart between the first discharge electrode and the second discharge electrode and delivering the second biphasic defibrillation pulse to the heart between the third discharge electrode and the fourth discharge electrode.

* * * * *